United States Patent
Koetsier et al.

(10) Patent No.: US 11,591,591 B2
(45) Date of Patent: Feb. 28, 2023

(54) ISOLATION OF HIGH MOLECULAR WEIGHT DNA USING BEADS

(71) Applicant: New England Biolabs, Inc., Ipswich, MA (US)

(72) Inventors: Paul A. Koetsier, Ipswich, MA (US); Barbara W. Taron, Essex, MA (US); Eric J. Cantor, Topsfield, MA (US)

(73) Assignee: New England Biolabs, Inc., Ipswich, MA (US)

( * ) Notice: Subject to any disclaimer, the term of this patent is extended or adjusted under 35 U.S.C. 154(b) by 261 days.

(21) Appl. No.: 16/547,844

(22) Filed: Aug. 22, 2019

(65) Prior Publication Data
US 2021/0054363 A1    Feb. 25, 2021

Related U.S. Application Data

(60) Provisional application No. 62/889,753, filed on Aug. 21, 2019.

(51) Int. Cl.
| C12N 15/10 | (2006.01) |
| B01L 3/00 | (2006.01) |
| B01L 9/06 | (2006.01) |

(52) U.S. Cl.
CPC ........ *C12N 15/1006* (2013.01); *B01L 3/5082* (2013.01); *B01L 9/06* (2013.01);
(Continued)

(58) Field of Classification Search
CPC .............. B01L 3/5021; C12N 15/1003; C12N 15/101; C12N 15/1013; C12Q 1/6804; C12Q 1/6806
See application file for complete search history.

(56) References Cited

U.S. PATENT DOCUMENTS

| 5,620,662 A * | 4/1997 | Perlman | B01D 21/262 422/550 |
| 6,221,655 B1* | 4/2001 | Fung | B01L 3/5021 435/7.1 |
| 6,255,477 B1 | 7/2001 | Kleiber et al. | |
| 2007/0248957 A1* | 10/2007 | Nova | G01N 35/00871 435/7.1 |

(Continued)

FOREIGN PATENT DOCUMENTS

| WO | 9811989 A1 | 3/1998 |
| WO | 0040697 A1 | 7/2000 |

OTHER PUBLICATIONS

Vogelstein et al., Proc Natl Acad Sci U S A. Feb. 1979;76(2):615-9. Preparative and analytical purification of DNA from agarose.

(Continued)

*Primary Examiner* — Jill A Warden
*Assistant Examiner* — Dwayne K Handy
(74) *Attorney, Agent, or Firm* — New England Biolabs, Inc.

(57) ABSTRACT

Provided herein is a method for isolating high molecular weight (HMW) DNA using beads that are at least 200 μm in diameter that utilizes a device for retaining the beads and where the purified DNA eluant exits the device without shearing the HMW DNA. In some embodiments, the method comprises precipitating the DNA onto the beads, washing the beads in the device, and then eluting the DNA from the beads therein while substantially avoiding shear. Compositions and kits for practicing the method are also provided.

10 Claims, 6 Drawing Sheets

(52) U.S. Cl.
CPC ............ *B01L 2200/0647* (2013.01); *B01L 2300/0609* (2013.01); *B01L 2300/12* (2013.01); *B01L 2300/16* (2013.01)

(56) References Cited

U.S. PATENT DOCUMENTS

| | | |
|---|---|---|
| 2009/0107927 A1 | 4/2009 | Belgrader et al. |
| 2010/0207051 A1 | 8/2010 | Fonnum et al. |
| 2011/0098462 A1 | 4/2011 | Ehwald et al. |
| 2013/0040834 A1* | 2/2013 | Bunce ............ G01N 35/1083 506/9 |
| 2013/0115637 A1* | 5/2013 | Baskakov ........ G01N 33/6896 435/7.92 |
| 2015/0119563 A1 | 4/2015 | Suh et al. |
| 2015/0132762 A1* | 5/2015 | Laugharn, Jr. ......... B02C 17/14 435/6.12 |
| 2018/0292399 A1* | 10/2018 | Verma ................ C12N 5/0609 |
| 2019/0010487 A1 | 1/2019 | Holmberg et al. |

OTHER PUBLICATIONS

Jakobi et al., Anal Biochem. Nov. 15, 1988;175(1):196-201. Filter-supported preparation of lambda phage DNA.

Steiner et al., Nucleic Acid Research (1995) 23:13, 2569-2570. A rapid one-tube genomic DNA extraction process for PCR and RAPD analyses.

Dederich et al., Nucleic Acids Res. Apr. 1, 2002; 30(7): e32. Glass bead purification of plasmid template DNA for high throughput sequencing of mammalian genomes.

Huanca-Mamani et al. Genetics and Molecular Research (2015), 14(3), 8001-8007. A simple, fast, and inexpensive CTAB-PVP-silica based method for genomic DNA isolation from single, small insect larvae and pupae.

Nanassy et al. Anal Biochem. Jun. 15, 2007;365(2): 240-245. Capture of genomic DNA on glass microscope slides.

Katevatis,e t al., (2017), Low concentration DNA extraction and recovery using a silica solid phase. PLoS ONE 12(5): e0176848.

Gene Link, DNA & RNA Precipitation Solutions, PS40-5132_PptionSoln_Ver3.1.doc, 2018.

Lam, et al Nat. Biotechnol. 2012 30: 771-776, Genome mapping on nanochannel arrays for structural variation analysis and sequence assembly.

Borman, et al., Mycopathologia, 169, 445-449, 2010.

Bott, et al., International Journal of Parasitology, 39-1277-1287, 2009.

Boom, et al., Journal of Clinical Microbiology, Mar. 1990, 28, 3, p. 495-503.

* cited by examiner

ISOLATION OF HIGH MOLECULAR WEIGHT DNA USING BEADS

CROSS REFERENCE

This application claims priority from U.S. Provisional Application No. 62/889,753 filed on Aug. 21, 2019, herein incorporated by reference.

BACKGROUND

Several methods exist to analyze long nucleic acid molecules. For example, nanopore sequencing is routinely used to sequence DNA molecules that are tens to hundreds of kilobases in length (see for example, Oxford Nanopore Technologies, Oxford UK). Read lengths in excess of two megabases (Mb) have been reported from one nanopore sequencing study (Payne, et al, Bioinformatics. 2019 35: 2193-2198). Likewise, the PacBio platform (Pacific Bioscience, Melo Park, CA) is capable of sequencing nucleic acid molecules that are tens of kilobases in length. Other genome mapping platforms such as the nanochannel array-based method (described by Lam, et al Nat. Biotechnol. 2012 30: 771-776, as developed by BioNano Genomics, San Diego, Calif.) also provide ways to analyze long nucleic acid molecules.

Long range genome analysis methods such as those described above require purified high molecular weight (HMW) DNA as an input. HMW genomic DNA (gDNA) has traditionally been purified from cells by phenol/chloroform extraction and subsequent alcohol precipitation while spooling the gDNA around a glass rod.

There are several methods for purifying HMW gDNA from small volume samples. These include magnetic discs, magnetic beads and silica filters. However, each of the existing methods have certain deficiencies. Some of the methods result in shearing of the HMW DNA. Other methods require multiple handling steps and therefore are not ideally suited to handling large numbers of samples at the same time. As the methods for HMW genome analysis improve and the number of clinical, diagnostic and research samples increase, there is a continued need to improve the reliability and efficiency of HMW DNA purification.

SUMMARY

Provided herein, among other things, is a method comprising: providing a composition comprising: (i) one or more beads, for example, glass beads, having a diameter of at least 200 micrometers (μm), (ii) a DNA solution comprising HMW DNA, for example, having a median size of at least 50 kilobases (kb); and (iii) a DNA precipitant that may, for example, be an alcohol such as ethanol or isopropanol and/or a high concentration chaotropic salt, or a high concentration of crowding reagent; incubating the composition to adhere the DNA to the one or more beads; removing unbound material from the one or more beads; washing the one or more beads with a wash buffer; releasing the DNA from the one or more beads into an elution buffer; and separating the released DNA from the one or more beads.

In some embodiments, the one or more beads may have a diameter in the range of 1 millimeter (mm) to 6 mm.

In some embodiments, the one or more beads may be 1-50 glass beads.

In some embodiments, the DNA solution is a prepurified HMW DNA. In some embodiments, the DNA solution is a complex mixture comprising HMW DNA and macromolecules. For example, in some embodiments the DNA solution may be a cell lysate. In some embodiments the DNA solution may be made by lysing cells to produce a lysate, centrifuging the lysate, and using the supernatant as the DNA solution. In other embodiments, the DNA solution may be made by lysing cells to produce a lysate and using the lysate as the DNA solution. In some embodiments, the DNA solution may be a lysate and may be produced by agitating cells in a lysis buffer at 300-2000 rpm at a temperature of at least 37° C.-56° C., wherein the speed of agitation determines the median length of the DNA used in step (a).

In some embodiments, the DNA precipitant may comprise a chaotropic salt, a crowding reagent such as Polyethylene glycol (PEG), and/or an alcohol such as ethanol or isopropanol.

In some embodiments, removing unbound material may be done by pouring or pipetting wherein pipetting utilizes for example, a wide bore pipette tip.

In some embodiments, the washing step may be done using an alcohol-containing wash buffer.

In some embodiments, the washing step may comprise a step that removes residual material from the DNA solution from the beads. The washing step may be done by washing beads in an alcohol-containing wash buffer, pouring beads into bead retaining tube, and spinning the bead retaining tube to remove the supernatant leaving behind DNA coated beads.

In some embodiments, releasing the DNA may be done by incubating the washed beads in an elution buffer to dissolve the DNA in the elution buffer. The beads and elution buffer may be contained in a bead retaining tube. The bead retaining tube may be centrifuged to permit the DNA containing elution buffer to be collected in a collection tube while the beads remain in the bead retaining tube. The bead retaining tube may have one or a plurality of exit openings where the openings have a diameter of less than the diameter of the one or more beads. The one more exit openings preferably has a diameter of at least 0.5 mm. The bead retaining tube is designed so that the one or more beads do not block the one or more exit openings so as to allow the flow of the bead containing eluant out of the bead containing tube. Alternatively, the beads and DNA elution buffer may be contained in a closed tube and the DNA containing elution buffer removed by pouring or pipetting the supernatant into a collection tube.

Also provided is a composition comprising: one or more glass beads having a diameter of at least 200 μm, a DNA solution comprising HMW DNA that has for example, a median size of at least 35 kb-50 kb and a DNA precipitant that may comprise an alcohol and/or chaotropic salts or a crowding reagent at high concentrations commonly used in the art. In some embodiments, the one or more glass beads have a diameter in the range of 1 mm to 6 mm. In some embodiments, the one or more glass beads is 1-50 glass beads. The DNA solution may be obtained from a cell lysate or may be a cell lysate or from HMW DNA previously purified with other methods. Where the DNA precipitant is an alcohol, the alcohol may be ethanol or isopropanol.

Also provided is a kit comprising: (a) beads (for example glass beads) that have a diameter of at least 1 mm; and (b) a bead retaining tube having one or more outlet openings having a diameter that is smaller than the beads but at least 0.5 mm. The bead retaining tube is designed so that the one or more outlet openings are not blocked by the beads. In some kits, the beads have a diameter in the range of 1 mm to 6 mm. Some kits may further comprise an outer collection tube, wherein the bead retaining tube fits in the outer tube.

The beads for use in the kit may be formed of a material that has a charged surface and that can be smooth or rough and wherein the beads may have any desired shape. In one example, the beads are made from glass or ceramic material and these beads may be spherical. 1-50 beads of size 1 mm-6 mm may be included with each bead retaining tube, where the number of beads may for example be inversely proportional to the size of the beads. The kit further comprises an outer tube, wherein the bead retaining tube fits into the outer tube wherein the outer tube has optionally a volume of 1 milliliter (ml)-2 ml. The kit may further comprise an elution buffer, an alcohol-containing wash buffer, a lysis buffer and/or enzymes (such as Proteinase K and RNase A) for lysing and/or purifying DNA in a DNA solution where the reagents and buffers described above may be provided in the same or different tubes or various combinations of tubes containing individual reagents and/or buffers and tubes containing mixtures of reagents and/or buffers.

BRIEF DESCRIPTION OF THE FIGURES

The figures and drawings are intended to illustrate one or more versions of the compositions and/or methods described herein. Unless stated otherwise, these are not intended to be limiting for the purpose of interpreting the scope of any claims.

FIG. 2A-2B show examples of bead retaining tubes and collection tubes, where the bead retaining tubes have at least one exit opening.

FIG. 3A-3B illustrates examples of 2 ml bead retaining tubes, which contain beads having a 4 mm diameter.

FIG. 4A-4B are diagrammatic representations of parts of the bead retaining tubes shown in FIG. 3A-3B.

DETAILED DESCRIPTION OF THE EMBODIMENTS

Unless defined otherwise, all technical and scientific terms used herein have the same meaning as commonly understood by one of ordinary skill in the pertinent art. Embodiments described herein may include one or more ranges of values (e.g., size, concentration, time, temperature). A range of values will be understood to include all values within the range, including subset(s) of values in the recited range, to a tenth of the unit of the lower limit unless the context clearly dictates otherwise. As used herein, the articles "a", "an", and "the" relate equivalently to a meaning as singular or plural unless the context dictates otherwise.

Figure 5:
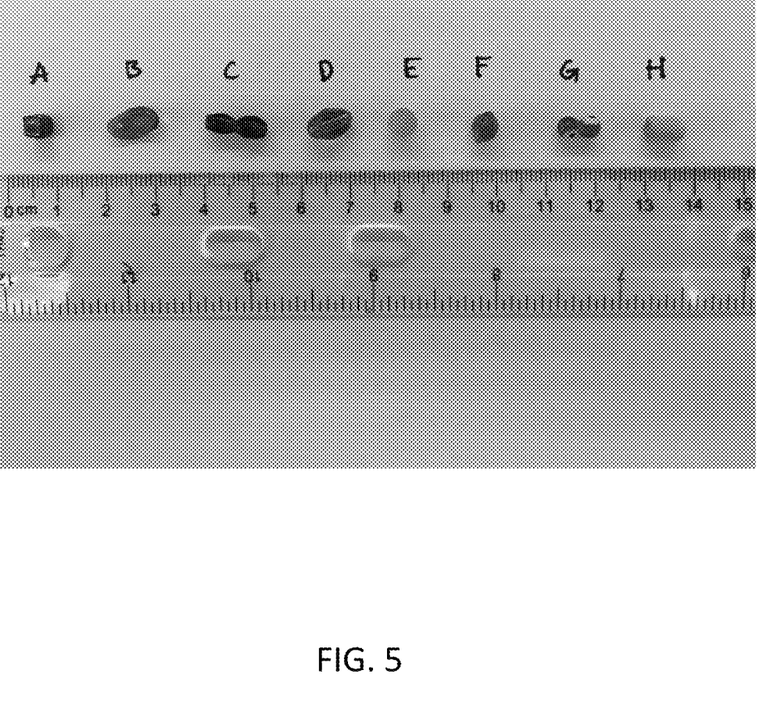
FIG. 5 shows that shape is not critical for beads where 8 different sized jewelry glass beads (A-H), were used and any shaped bead of appropriate format can serve as binding matrix. Results are shown in Table 4.

Provided herein is a method for isolating HMW DNA. The method uses beads, which have a surface around which the HMW DNA can be wrapped. The solid surface is preferably spherical but can also be other shapes without limitation. Some examples of various bead shapes that were tested and found effective are provided in Table 4 and FIG. 5. The material of the beads is preferably glass for reasons of cost and ease of availability. However, any material that has a charge, is polar, has a rough surface or is in any form sticky for DNA is also suitable for the beads. The charged surface enables the DNA to adhere to the beads. Such materials include ceramics and clay. Moreover, although transparent glass beads are used in the examples, Table 4 and FIG. 5 provides data on colored glass that works effectively too. The size of the beads may vary according to the length of DNA intended for purification. Beads with a diameter of at least 1 mm are preferred for reasons that include that they can be manually handled by means of tweezers for placing the beads in the tubes. Beads less than 200 μm should be avoided. Below 200 μm, the beads can move against each other to cause undesirable shear damage to the DNA adsorbed to their surface.

When 2 ml tubes are used for sample processing, the total surface area of the beads per tube or sample may be in the range of 75 $mm^2$ to 150 $mm^2$ in some cases. For example, if bead having a diameter of 4 mm is selected, then two beads can be used per 2 ml tube/sample. In this example, the total surface area of the beads is 100.54 $mm^2$. If smaller beads are selected (e.g., beads that have a diameter in the range of 200 μm to 4 mm) then more beads should be used. The following table describes the relationships between diameter, surface area/bead, bead number to obtain a total bead surface area of approximately 100 $mm^2$ and weight of borosilicate beads (which have mass/volume of 2.23 milligram (mg)/mm$^3$) to obtain the same.

TABLE 1

| Bead Diameter | Surface Area/ Bead (mm2) | Number of Beads | mg Beads |
|---|---|---|---|
| 0.25 | 0.2 | 500 | 9.1 |
| 0.5 | 0.79 | 127 | 18.4 |
| 1 | 3.14 | 32 | 37.1 |
| 2 | 12.57 | 8 | |
| 3 | 28.27 | 4 | |
| 4 | 50.27 | 2 | |
| 5 | 78.54 | 1 | |
| 6 | 113.1 | 1 | |

Where large molecules of DNA are desired from a relatively small sample of a cell lysate or tissue biopsy for example, it may be desirable to use beads in the 1 mm to 6 mm range in a tube capable of holding about 1 ml-2 ml where the number of beads, in one example, may have a total surface area of at least about 100 mm$^2$. This may be achieved using up to 30-50 beads of 1 mm in diameter. Larger number of beads may be used if the bead size is smaller while remaining greater than 200 µm. For example, one bead of 5 mm or 6 mm diameter may be used, two beads of 4 mm diameter may be used, four beads of 3 mm diameter may be used, eight beads of 2 mm diameter may be used, or 32 beads of 1 mm diameter may be used to achieve a 100 mm surface area. Where a sample is in a volume greater than 2 ml, the size of the bead retaining tube, collection tube and the available surface area for a preferred size and number of beads can be scaled accordingly.

Figure 2A:
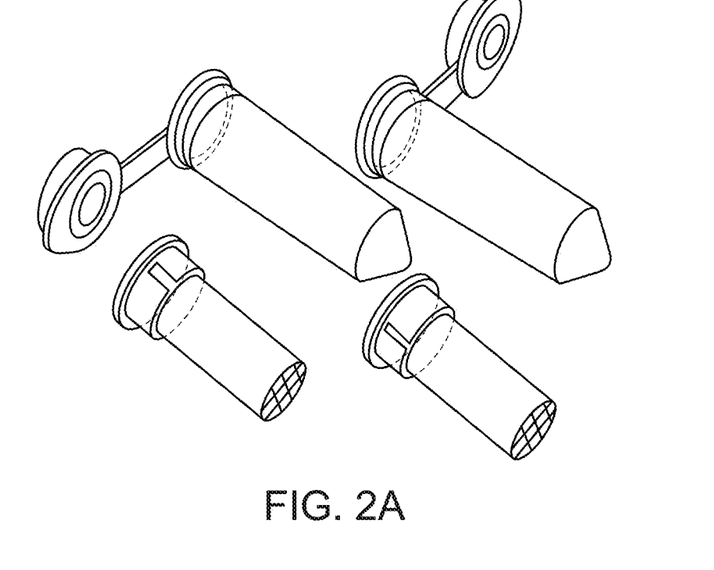
FIG. 2A illustrates flat bottomed bead retaining tubes that could be used in the present method and separately the collection tube suitable in design for all steps of the method.
Figure 2B:
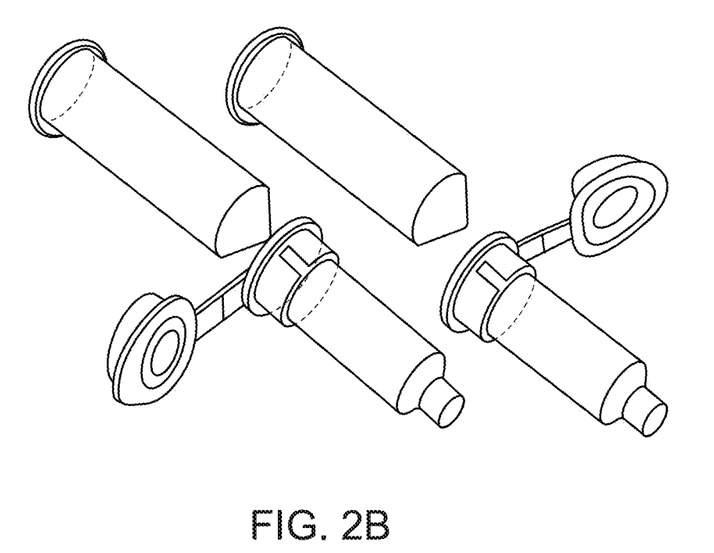
FIG. 2B illustrates 2 ml bead retaining tubes that have one collar that could be used in the present method and separately the collection tube suitable in design for all steps of the method.

As described below, certain tubes used for various steps of the method may have some particular characteristics that are advantageous. For example, for small samples of about 2 ml or less, microfuge tubes are preferable as these can be used in a microcentrifuge. In addition, as shown in FIG. 2A-2B, an inner tube (here referred to as a bead retaining tube) contains at least one exit opening that can be inserted into an outer tube (collection tube). The outer tube may be a microfuge tube.

Where the method comprises precipitating the DNA onto the beads, washing the beads, and then eluting the DNA from the beads, the separation of eluted DNA from the beads can be achieved conveniently and effectively through the one or more exit openings in the base of the bead retaining tube where the elution and separation of DNA into a collection tube can be enhanced using centrifugation. The size of the exit opening should be less than the diameter of the beads to enable separation of DNA from the beads. The one or more exit openings in the bead retaining tube are each preferably at least 0.5 mm so as to avoid shearing of the HMW DNA passing through these exit openings. Where exit openings are, for example, 0.5 mm in diameter, the beads may be at least slightly larger than 0.5 mm and where the exit opening is for example 1 mm, the beads will be at least slightly larger than 1 mm in diameter.

Examples of two types of tubes with at least one exit opening are provided here for use in method steps.

Figure 3A:
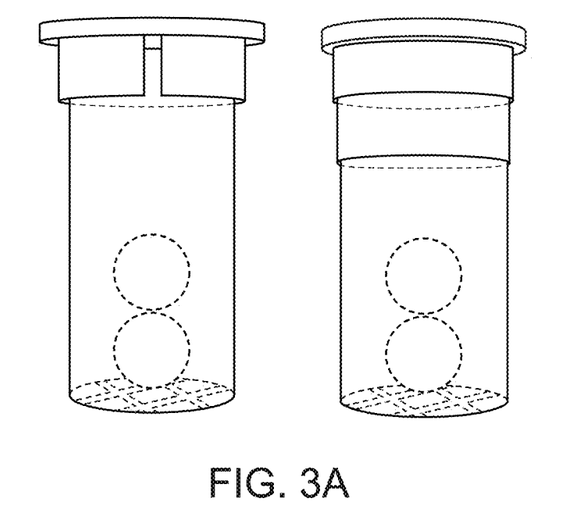
FIG. 3A shows a perspective view of one example of 2 ml bead retaining tubes, having a flat-bottom with a plurality of openings containing the 4 mm beads.
Figure 3B:
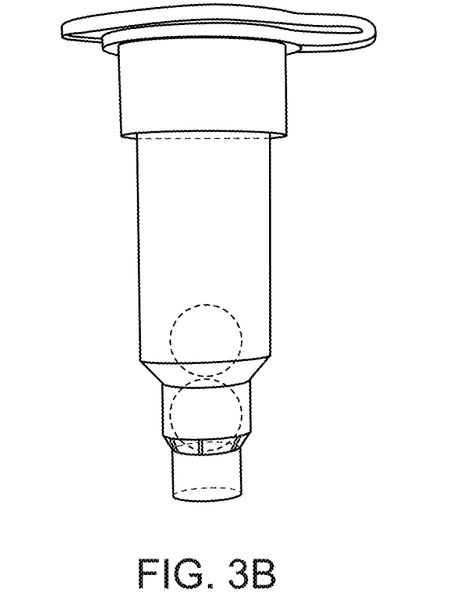
FIG. 3B shows a perspective view of one example of a bead retaining tube having two collars and containing beads having a 4 mm diameter.
Figure 4A:
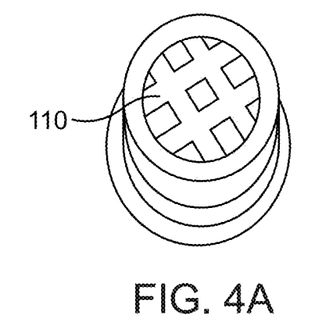
FIG. 4A shows that the flat exit opening containing a plurality of exit holes 110 each being at least 0.5 mm in diameter at the base of a bead collection tube shown in FIG. 3A.
Figure 4B:
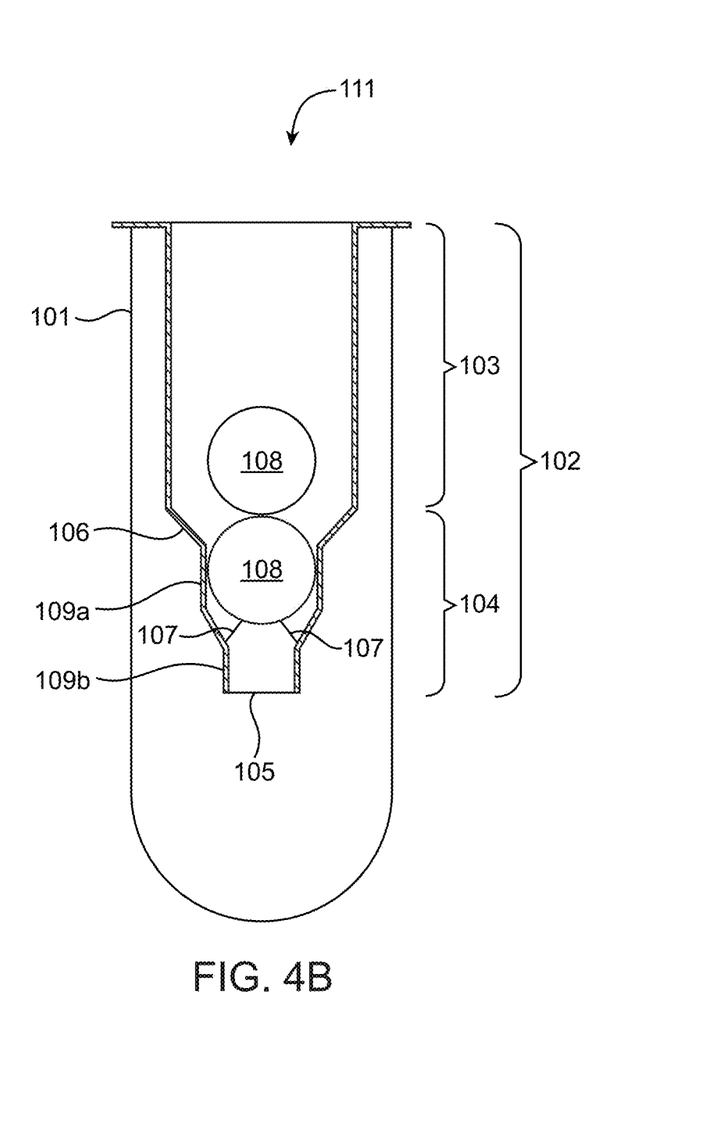
FIG. 4B shows the two collared bead retaining tube in FIG. 3B contained in a collection tube. Bead retaining tube 102 is contained within collection tube 101. Bead retaining tube body is 10. Collar body 104, including collars 109*a*4 and 109*b* of decreasing size, are shown where exit opening 105 is greater than 0.5 mm in diameter. Sloping tube side 106 provide a transition to narrower collar 104. Two ridges 107 are shown on which one or a plurality of beads 108 sit to permit DNA in the eluant to flow into the collection tube and avoid blocking the exit opening. An opening 111 at the top of bead-retaining tube is oppositely placed with respect to the exit opening 105 at the bottom of tube, where opening 111 is used for accepting the DNA solution and the beads.

The first example is a bead retaining tube 102 into which DNA containing beads 108 are placed through opening 111 and contains collars 109a and 109b with exit opening 105 as shown in FIG. 4B. The bead retaining collar has a shape that is preferably not tapered but may be cylindrical or part cylindrical and optionally the wall of the cylindrical collar between the bead containing body of the bead and the exit opening may be partially cut away. One cylindrical collar is shown on the tubes in FIG. 2A and two collars are shown in FIGS. 3B and 4B. In FIGS. 3B and 4B, at least the ultimate bead retaining collar 109b has a reduced diameter compared to the bead containing portion of the tube. The beads are prevented from entering the ultimate collar 109b with exit opening 105 because of size of the entry aperture being smaller than the bead diameter. Any number of collars having any desired shape that does not result in shearing of the DNA may be used. The collar may be replaced by any other bead retaining structure associated with the exit opening that permits eluted DNA to pass through without shear. In addition, it is a preferred feature of the bead retaining tube that the beads do not block the exit opening. This may be achieved here by a plurality of internal projecting ridges or spacers 107 that are positioned on or near the bead retaining collar where the number of ridges may for example include 3 or 4 protruding ridges that are evenly spaced and onto which the beads or a bead may sit providing space for DNA containing eluate to flow around. Other numbers of ridges and their distribution or other protruding structures for holding beads having a selected size preferably at least 1 mm may be selected allowing the DNA eluant to flow around the beads and enter the collection chamber through the exit opening. In this way DNA containing eluant can flow easily into a collection tube (101) by gravity or with the aid of a centrifugation step. The one or more exit openings of a bead retaining tube may have an internal spacer or ridge that spaces the beads from the exit opening during centrifugation.

The interface between collar and the bead containing body of the bead retaining tube (106) may be sloping for example at a 45° angle or curved so as to minimize shear as the DNA eluant passes into the collection tube.

In the second example of a bead retaining tube containing the beads, separation of HMW DNA from the beads may not utilize a collared exit funnel. Instead, the tube may have a flat bottom with a grid or plurality of exit openings (110) each opening having a size of at least 0.5 mm allowing the beads having a greater size to remain in the tube while the eluant containing DNA flows through without obstruction (see FIG. 3A-3B). This contrasts with conventional use of the fine membranes and frits in silica-based DNA preparation methods that have pore sizes less than 0.5 mm and cause unwanted shearing of HMW DNA.

If bead sizes of less than 0.55 mm but at least 200 µm are used for HMW purification, it is recommended that a batch method is used where a tube that does not have an exit opening is used for the elution step and after release of the DNA from the beads, the supernatant containing the DNA is removed using a wide bore pipette tip.

The present method avoids many of the limitations of conventional methods of DNA purification for HMW DNA molecule purification. The present method does not require vortexing or that the DNA sample pass through any fine holes, or the use of beads having a diameter of less than 200 µm such as commercially available magnetic beads, thereby eliminating many sources of shearing that are associated with other methods (see for example, Jakobi, et al., Anal Biochem., 175(1):196-201, 1988; U.S. Pat. No. 6,255,477; Nanaassy, et al. Anal Biochem., 365(2), 2007: 240-245; Steiner, et al., Nucleic Acid Research, 23:13, 2569-2570 1995; and Vogelstein, et al., PNAS, 76:2, 615-619, 1979). The median length of the isolated gDNA produced by the present method is at least 50%, at least 70% or preferably at least 90% of the median length of the input DNA. The method can be used to purify HMW DNA from virtually any type of DNA sample, e.g., isolated white blood cells, cultured cells, cells from a biopsy, and bacterial cells, or previously purified HMW extracted with other methods, etc.

The gDNA isolated by the present method can be analyzed using any of a wide range of long-range analysis methods, including long read DNA sequencing and genotyping.

The term "long DNA" and "high molecular weight (HMW) DNA" refer to DNA that is generally larger than 30-50 kb for example at least 50 kb, for example as much as 100 kb, 200 kb, 300 kb, 500 kb, or 1 Mb. Although the present methods are particularly suited to obtaining HMW DNA, the methods may be used for obtaining shorter DNA also.

The term "DNA precipitant" refers to: a high salt concentration of a chaotropic salt; an alcohol; and/or a crowding agent. While not wishing to be limited by theory, a chaotrope can be used to precipitate DNA because nucleic acids are covered by a shell of hydration consisting of water molecules that maintain the solubility of DNA in aqueous solutions. With the addition of chaotropic ions to the nucleic acid, this relatively ordered structure of water molecules of the hydrate shell is destroyed. The chaotropic salts create a hydrophobic environment for DNA precipitation. As a further feature of the chaotropic salts, the respective cations saturate the beads with positive charges, which still improves the binding of nucleic acids under hydrophobic conditions. Chaotropic salts increase the solubility of nonpolar substances in water. They denature proteins because they have the ability to disrupt hydrophobic interactions. They do not denature DNA or RNA. Examples of chaotropic salts used in DNA purification include guanidine chloride and guanidine thiocyanate. For example, Promega describes the use of high concentrations of chaotropic salts (e.g. guanidine chloride HCL) to cause DNA to selectively bind to silica membranes. Promega also offers a kit called Reliaprep™ (Promega Corporation, Madison, Wis.) where the gDNA is bound to the membrane (in the case a cellulose material) with the help of a crowding reagent (PEG). This kit does not use chaotropic salts or alcohol as a precipitant. Chaotropic guanidinium thiocyanate (GuSCN) enhanced DNA-silica adsorption was described by Katevatis et al., 2017 PLOS ONE 12(5): e0176848. Other examples of DNA precipitants are provided by GeneLink (DNA & RNA Precipitation Solutions). Adding ethanol decreases the dielectric constant of the solution. In some embodiments, the method may involve producing a composition comprising one or more beads (as described above)(e.g., 1-50 glass beads) that have a diameter of at least 200 μm, a DNA solution comprising DNA that has a median length of at least 50 kb, e.g., gDNA that has a median length of at least 50 kb, at least 200 kb, at least 500 kb or at least 1 Mb and a DNA precipitant (e.g., a high concentration of chaotropic salts and/or ethanol or isopropanol, with or without salt, wherein the precipitant in the composition at a concentration and pH that will cause precipitation of the DNA). The precipitated DNA adheres to the surface of the one or more beads and may appear to form a loose gel that encapsulates each of the beads that becomes more tightly associated with the beads during the washing steps that follow precipitation.

After the DNA has been adhered to the beads, the unbound material (which remains in the liquid surrounding the beads) can be removed in way that avoids disturbing the one or more beads. This can be done by pipetting or aspiration, for example. Next, the one or more beads are washed in a wash buffer, e.g., an alcohol containing wash buffer such as 70% ethanol or the like. This step can be done by, for example, adding a volume of the wash buffer to the beads in a container, gently inverting the container, and then carefully removing the wash buffer without unduly disturbing the one or more beads. If necessary, any residual wash buffer can be removed by centrifugation. This may be done, for example, by decanting the beads and residual wash buffer into a bead retaining tube, and then centrifuging the beads while they are in the column. In these embodiments, the residual wash buffer should pass through a plurality of holes of at least 0.5 mm at the bottom of the column, leaving the washed beads in the bead retaining tube.

Next, the DNA may be released from the beads into an elution buffer. This may be done by transferring the beads to another container, adding a volume of elution buffer (e.g., a Tris/EDTA solution or other buffers known to release DNA (see for example, Katevatis, et al., (2017)) to the beads, and then incubating the beads, e.g., for 5-10 minutes at room temperature or at an elevated temperature (e.g., 37-56° C.) to elute the DNA from the beads.

Next, the eluted DNA is separated from the one or more beads. This step may be done by decanting the DNA containing beads into a bead retaining tube that is within a collection tube, adding elution buffer to release the DNA and centrifuging the beads while they are in the tube. In these embodiments, the eluate passes through the exit opening or openings at the bottom of the bead retaining tube into the collection tube. The eluted DNA, which is now in the collection tube, can then be stored, further processed, or analyzed directly.

The DNA solution may comprise, for example, purified gDNA in water or buffer, a complex mixture comprising DNA and biological macromolecules, a cell lysate, or a cell lysate that that has been subjected to a clean-up procedure. The gDNA may be extracted from a tissue or a powdered form thereof. However, the DNA solution is prepared, the sample may be treated with a proteinase (e.g., Proteinase K) to digest the protein in the sample. The method may or may not include a phenol-chloroform extraction step to remove protein prior to further purification. In some embodiments, the DNA sample may be prepared by incubating cells in a lysis buffer and treating the lysate with a protease such as Proteinase K. Any cell lysis may be done with or without agitation, where the speed of agitation determines the median length of the resultant gDNA (see for example, FIG. 6).

The DNA solution may contain gDNA from any organism, e.g., plants, animals (e.g., reptiles, mammals, insects, worms, fish, etc.), tissue samples, bacteria, fungi (e.g., yeast), viruses, etc. In certain embodiments, the DNA used in the method may be derived from a mammal, wherein in certain embodiments the mammal is a human. In exemplary embodiments, the DNA sample may contain gDNA from a mammalian cell, such as, a human, mouse, rat, or monkey cell. The sample may be made from cultured cells or cells of a clinical sample, e.g., a tissue biopsy scrape or lavage, for example.

Figure 6:
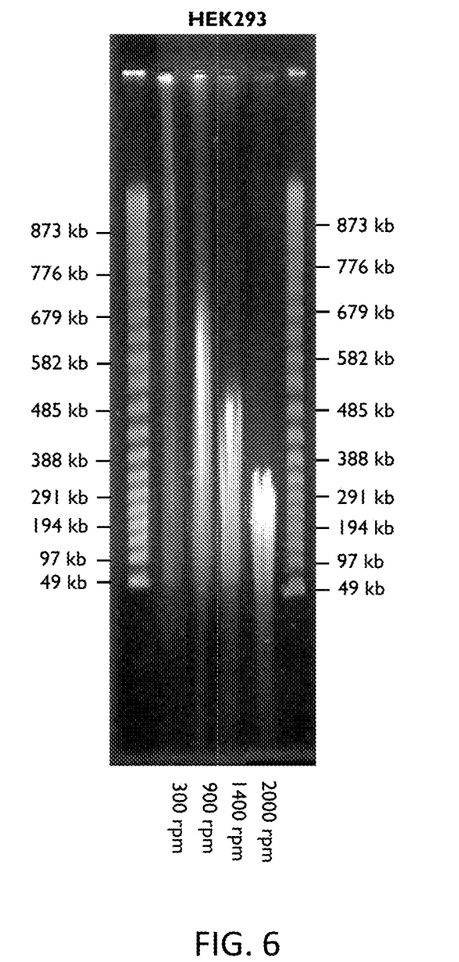
FIG. 6 shows the size ranges of gDNA isolated from human embryonic kidney 293 (HEK293) cells at various agitation speeds during the lysis protocol prior to purification. HMW gDNA from $1 \times 10^6$ HEK293 cells was isolated according to the protocol for cultured mammalian cells as described in Example 1. During lysis samples were agitated at different agitation speeds (300 rpm, 900 rpm, 1400 rpm and 2000 rpm). 300 nanograms (ng) of each sample was loaded on a 0.75% pulsed field agarose gel using 0.5×KBB buffer and a Pippin Pulse™ electrophoresis power supply (Sage Science, Inc, Beverly Mass.). A molecular weight marker the Lambda PFG Ladder (New England Biolabs, Ipswich, Mass.) was used. An agitation speed of 300 rpm resulted in largest gDNA and an agitation speed of 2000 rpm resulted in DNA that was no larger than 300 kb.

The eluted DNA may be analyzed using any suitable method. Table 4 shows the results of a spectrophotometric analysis. FIG. 6 shows a gel of sizes of DNA after agitation during lysis incubation at different speeds.

In some embodiments, the eluted DNA may be sequenced using a long read single-molecule sequencing approach such as nanopore sequencing (e.g. as described in Soni, et al Clin Chem 53: 1996-2001 2007, and developed by Oxford Nanopore Technologies) or Pacific Biosciences' fluorescent base-cleavage method (which currently has an read length of tens of kilobases, with some reads over 100 kb). Alternatively, the eluted DNA may be analyzed by other long-range genome mapping methods, such as the nanochannel array-based method (described by Lam, et al., Nat. Biotechnol. 2012 30: 771-776, as developed by BioNano Genomics, San Diego, Calif.)).

Compositions

A variety of compositions that are made during practice of the method are also provided. In some embodiments, the composition may contain one or more beads (e.g., 1-50 beads) where for example, the beads are glass beads. The beads are required to have a diameter of at least 200 µm (e.g., one or more beads have a diameter in the range of 1 mm to 6 mm). The composition further includes a DNA solution comprising HMW DNA that has, for example, a median size of at least 50 kb; and a precipitant comprising alcohol, e.g., ethanol or isopropanol, with or without salt. In these embodiments, the components are in the same container, e.g., a 1.5 ml or 2 ml microcentrifuge tube although any size tube may be utilized according to the volume of the sample. The DNA solution may be made from a cell lysate, e.g., bacterial or mammalian cells, for example. In alternative embodiments, a composition may comprise one or more beads (e.g., 1-50 beads in a 2 ml tube) that have a diameter of at least 200 µm (e.g., one or more beads have a diameter in the range of 1 mm to 6 mm). In these embodiments, the DNA is adhered to the surface of the beads. In these embodiments, the components may be within a bead containing tube with a top opening for receiving sample and beads and an exit opening for releasing a DNA aqueous solution eluted from beads, into a collection tube.

Kits

Figure 1:
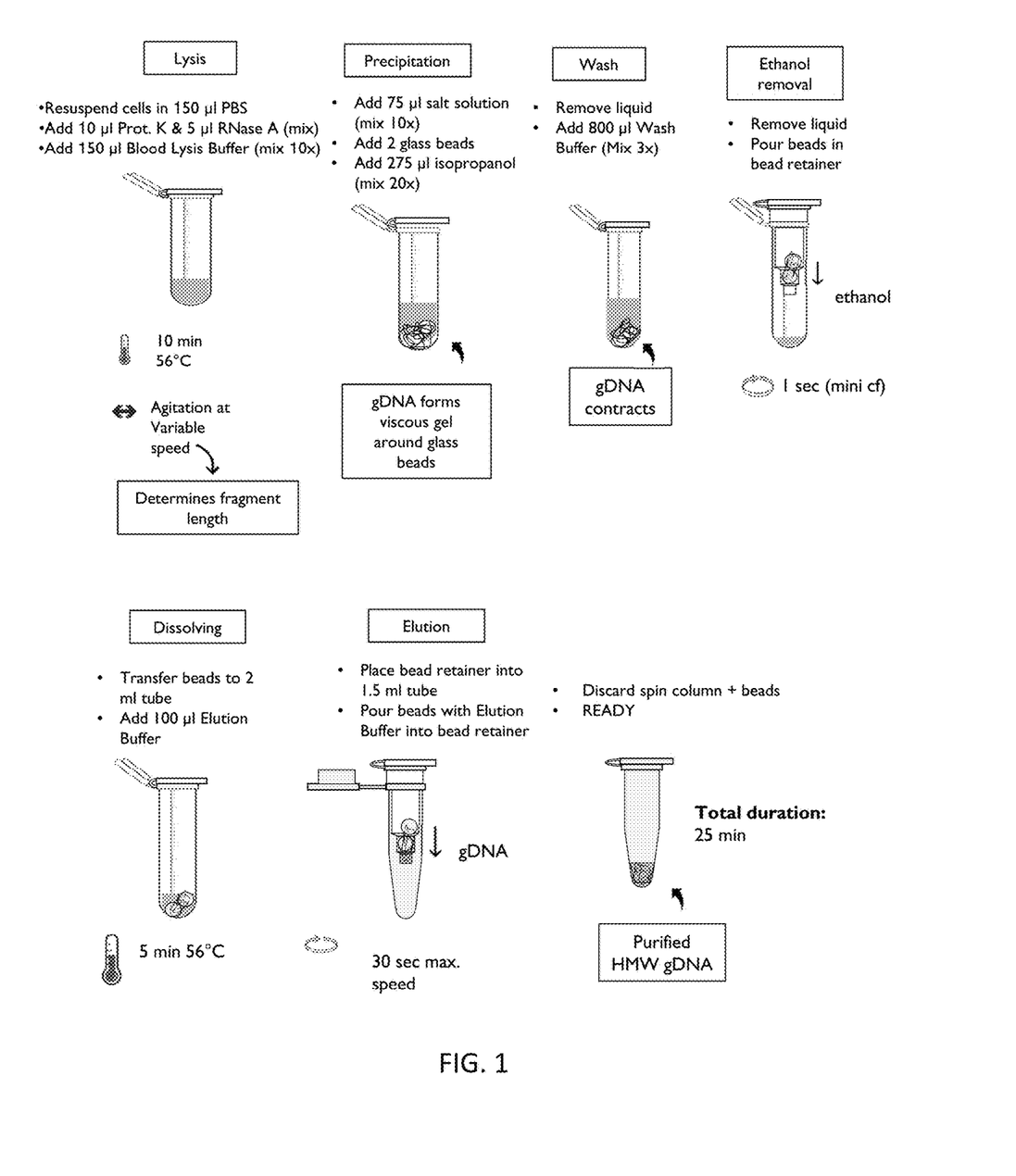
FIG. 1 schematically illustrates an example of how HMW gDNA can be isolated and purified from mammalian cells using the present method.

Also provided by this disclosure are kits for practicing the subject method, as described above. In some embodiments, the kit may contain any one or more of the components listed above. For example, a kit may contain (a) one or more beads that have a diameter of at least 1 mm (e.g., one or more beads that have a diameter in the range of 1 mm to 6 mm), and (b) a bead retaining tube having one or more outlet openings having a diameter that is smaller than the beads, and wherein the bead retaining tube is designed so that the one or more exit openings are not blocked by the one or more beads during use. Details of examples of bead containing tubes that may be included in the kit are provided above. In some embodiments, a kit may additionally contain an outer tube (collection tube), wherein the bead retaining tube fits in the outer tube as illustrated in FIG. 1 and FIG. 4B. The outer tube may be a standard 1.5 ml or 2 ml microcentrifuge tube. In addition, a kit may further comprise one or more buffers such as a lysis buffer for lysing a biological sample containing cells, a protein removal solution, a wash buffer (e.g., an alcohol-containing wash buffer) for washing the DNA adhered beads and an elution buffer for removing DNA from beads. The beads may be glass beads.

The various components of the kit may be present in separate containers or certain compatible components may be pre-combined into a single container, as desired. In addition to above-mentioned components, the subject kits may further include instructions for using the components of the kit to practice the subject methods, i.e., to instructions for sample analysis.

All publications, patents, and patent applications mentioned in this specification are herein incorporated by reference to the same extent as if each individual publication, patent, or patent application was specifically and individually indicated to be incorporated by reference. This includes U.S. Provisional Application No. 62/889,753 filed on Aug. 21, 2019.

EXAMPLES

Aspects of the present teachings can be further understood in light of the following examples, which should not be construed as limiting the scope of the present teachings in any way.

Example 1: Preparation of Deproteinized DNA Samples from Lysates (a) Preparation of HMW DNA from a Suspension of Cells.

Lymphocytes were obtained from whole blood as a pellet after centrifugation using standard techniques. The pellet was resuspended in phosphate buffered saline (PBS). Alternatively, cultured cells (HEK293) were obtained from cell culture.

The $5 \times 10^6$ cells in 150 microliters (up of PBS were then treated with 5 µl RNase A (20 mg/ml) and 10 µl of Proteinase K (20 mg/ml). 150 µl of Monarch® DNA Blood lysis buffer (New England Biolabs, Ipswich, Mass.) was added and the cells incubated for 10 minutes at 56° C. while shaken at 500-2000 rpm depending on the length of DNA required. For Mb DNA, it was found that 500 rpm was a maximum shaking speed. For 100 kb-250 kb DNA, 1400-2000 rpm was used (see FIG. 6). Since substantially all the protein was digested, a protein removal step was not required prior to the isolation of the HMW DNA.

(b) Preparation of HMW DNA from Solid Tissue.

10 mg of tissue were prepared first by crushing in a micropestle (1.5 ml tube). Lysis buffer containing Proteinase K (10 µl of a solution of 20 mg/ml) plus 300 µl of buffer containing 50 mM Tris, 2% SDS, 100 mM NaCl and 20 mM EDTA pH 88.25 was added so as to digest the protein in the sample. The sample was incubated at 56° C. for 45 minutes in a shaker. The shaking speeds were as described in (a). 10 µl RNase A was then added (20 mg/ml) and incubated 56° C. for 10 minutes. Protein was separated from DNA by a chloroform/phenol step. The aqueous phase (400 µl) was recovered using a 1000 µl wide bore pipet tip and transferred to a 2 ml tube for precipitation of the HMW DNA.

TABLE 2

Examples of tissues with some alternative amounts, volumes of lysis buffer, Proteinase K and yield of DNA.

| Sample type | Amount (mg) | Tissue Lysis Buffer (µl) | Proteinase K (µl) | Expected yield (µg) |
| --- | --- | --- | --- | --- |
| Muscle/fibrous tissue | Up to 10 | 300 | 10 | 3-4 |
| | Up to 20 | 600 | 20 | 12-14 |
| Brain | Up to 10 | 300 | 10 | 3 |
| | Up to 20 | 600 | 20 | 6 |
| DNA-rich/soft organ tissue | Up to 5 | 300 | 10 | 5-15 |
| | Up to 10 | 600 | 20 | 10-30 |
| Rodent tail | Up to 10 | 300 | 10 | 10-15 |
| | Up to 20 | 600 | 20 | 20-30 |

(c) Preparation of HMW DNA from microbes

At least $2 \times 10^9$ microbes were pelleted and resuspended in a lysis buffer containing 10 µl lysozyme (25 mg/ml), and 300 µl of tissue lysis buffer (50 mM Tris, 2% SDS, 100 mM NaCl and 20 mM EDTA pH 8.25) and incubated at 37° C. at 1400-2000 rpm for 3-5 minutes. 20 µl of Proteinase K was then added and incubated at 56° C. for a minimum of 30 minutes in a thermal mixer at maximum speed (1400-2000 rpm). 10 µl of RNase A was then added and incubated for 10 minutes at 56° C. Protein was separated from DNA by a chloroform/phenol step. The aqueous phase was recovered using a 1000 µl wide bore pipet tip and transferred to a 2 ml tube for concentration of the HMW DNA.

TABLE 3

Preparation of deproteinized DNA samples from microbial lysates

| Number of bacterial cells | PBS (µl) | Tissue Lysis Buffer (µl) | Proteinase K (µl) |
|---|---|---|---|
| Up to $2 \times 10^9$ | 150 | 150 | 10 |
| Up to $5 \times 10^9$ or unknown number | 300 | 300 | 20 |

Example 2: Concentration of High Molecular Weight DNA

The following protocol describes an example of how HMW gDNA was isolated from a DNA sample using capture beads. As shown in Table 4, different sized and shaped beads made of various materials to which DNA absorbs can be used for this protocol while avoiding beads less than 200 µm that increases DNA shear and avoiding any form of filter with a pore size of less than 0.5 mm.

Samples described in FIG. 1 including lysates of blood samples or cultured cells or the non-protein phase of the deproteinated solid tissue or microbe sample were used in the following steps. The sample size was either 400 µl or 800 µl Two DNA glass capture beads were added to each sample in a 2 ml tube.
  (a) Binding of DNA to beads and removing contaminants by washing:
      275 µl of isopropanol (low input sample) or 275 µl isopropanol and 275 µl ethanol (high input sample) was then added to the sample to precipitate the DNA onto the capture beads.
  (b) Washing the beads to remove DNA precipitant and lysate contaminants: 800 µl of 70% ethanol was added to the sample. The wash buffer that contained a final concentration of 70% ethanol caused DNA to bind more tightly to the beads. The wash buffer was then decanted, and the beads were poured into an empty tube insert with an exit funnel (collar with exit opening) or porous mesh (pore size at least 0.5 mm) at the bottom of the tube. The collar with exit opening was designed so that the beads would not block the out flow of eluent. This was achieved by ridges on the collar of the exit funnel. The empty tube insert was placed into an empty 1.5 ml centrifuge tube. Examples of bead retaining tubes that can be used in the present method are shown in FIGS. 2A-B, 3A-B and 4A-B.
      The wash buffer was removed in a centrifugation step and was then repeated.
  (c) Elution of DNA from beads in a concentrated solution:
      The dried beads containing the HMW DNA were poured into a 2 ml tube. Elution buffer (e.g., Tris EDTA) was added and incubated for 5-10 minutes at 56° C. in a thermal mixer with agitation at lowest speed (300 rpm) or in heat block to permit the elution of DNA from the beads. The eluated DNA solution and the beads were transferred to a bead retaining tube positioned in a 1.5 ml microfuge tube. The tube insert seated in the centrifuge tube was then centrifuged for 0.5 minutes at a max speed (>12,000×g) to allow the gDNA to be collected in the centrifuge tube. The tube insert with glass beads was then discarded.

The samples contained HMW DNA and were stored at 4° C. The amount and purity of the DNA collected by this method was analyzed. Various borosilicate bead sizes, shapes and materials were tested, and the results are shown in Table 4. All beads functioned well as a binding matrix for gDNA providing similar yields for all types of glass beads. Beads of 1 mm and 2 mm diameter were collected in a flat bottom spin column from Corning, Inc. (Corning, N.Y.) with openings of 0.5 mm max. All larger beads and the jewelry beads were collected in flat bottom spin columns from Corning, Inc. with openings of 1.5 mm max diameter.

TABLE 4

| # | Bead type | No. of beads | Nucleic Acids (ng/µl)* | Yield (ug) | Background (A260) | Residue (%) | A260/A280 | A260/A230 |
|---|---|---|---|---|---|---|---|---|
| 1 | 212-300 micron | 500 (9.1 mg) | 76.2 | 7.6 | 0 | 0.7 | 1.85 | 2.12 |
| 2 | 212-300 micron | 500 (9.1 mg) | 67.4 | 6.7 | 0 | 0.8 | 1.85 | 2.29 |
| 3 | 425-600 micron | 127 (18.4 mg) | 76.1 | 7.6 | 0 | 0.8 | 1.85 | 2.31 |
| 4 | 425-600 micron | 127 (18.4 mg) | 72.3 | 7.2 | 0 | 0.8 | 1.86 | 1.98 |
| 5 | 1 mm | 32 (37.1 mg) | 63.5 | 6.4 | 0 | 0.9 | 1.87 | 2.40 |
| 6 | 1 mm | 32 (37.1 mg) | 77.5 | 7.8 | 0 | 1.3 | 1.87 | 2.48 |
| 7 | 2 mm | 8 | 75.7 | 7.6 | 0 | 0.8 | 1.88 | 2.41 |
| 8 | 2 mm | 8 | 79.0 | 7.9 | 0 | 0.9 | 1.86 | 2.43 |
| 9 | 3 mm | 4 | 65.0 | 6.5 | 0 | 3.6 | 1.85 | 2.91 |
| 10 | 3 mm | 4 | 69.5 | 7.0 | 0 | 2.1 | 1.89 | 2.61 |
| 11 | 4 mm | 2 | 78.6 | 7.9 | 0 | 1.3 | 1.87 | 2.51 |
| 12 | 4 mm | 2 | 80.0 | 8.0 | 0 | 0.6 | 1.90 | 2.39 |
| 13 | 5 mm | 1 | 73.1 | 7.3 | 0 | 0.7 | 1.83 | 2.35 |
| 14 | 5 mm | 1 | 78.9 | 7.9 | 0 | 0.7 | 1.88 | 2.33 |
| 15 | 6 mm | 1 | 81.6 | 8.2 | 0 | 1.0 | 1.89 | 2.26 |
| 16 | 6 mm | 1 | 76.5 | 7.7 | 0 | 0.9 | 1.90 | 2.27 |
| 17 | rectangular black glass bead | 1 | 75.6 | 7.6 | 0.25 | 0.6 | 1.86 | 2.55 |
| 18 | long disc shaped green glass bead | 1 | 80.1 | 8.0 | 0 | 0.8 | 1.88 | 2.40 |

TABLE 4-continued

| # | Bead type | No. of beads | Nucleic Acids (ng/μl)* | Yield (ug) | Background (A260) | Residue (%) | A260/A280 | A260/A230 |
|---|---|---|---|---|---|---|---|---|
| 19 | 8-shaped long green glass bead | 1 | 71.2 | 7.1 | 0.71 | 7.5 | 1.74 | 4.02 |
| 20 | double hexagonal shaped violet glass bead | 1 | 78.8 | 7.9 | 0.35 | 1.3 | 1.85 | 2.40 |
| 21 | blue glass bead | 1 | 80.9 | 8.1 | 0 | 1.1 | 1.89 | 2.28 |
| 22 | double hexagonal shaped small orange glass bead | 1 | 77.4 | 7.7 | 0 | 1.4 | 1.90 | 2.32 |
| 23 | 8-shaped orange with eyes glass bead | 1 | 83.1 | 8.3 | 0.85 | 1.2 | 1.81 | 2.25 |
| 24 | cylinder shaped glass bead | 1 | 82.6 | 8.3 | 0.93 | 2.6 | 1.79 | 2.31 |

*The amount of DNA was determined from 2 μl samples using Trinean DropSense ® 16 spectrophotometer (Unchained Labs, Woburn, MA)

As shown in the table above, all large size beads worked well for isolating HMW gDNA from cultured cells. Beads ranging from 1 mm-6 mm were identified as being most practical, since they could be placed into in bead retaining tubes with large sieve openings, which allows for a convenient separation of the beads and the gDNA containing eluate by centrifugation in a microcentrifuge without shearing the gDNA. In addition, in these bead retaining tubes traces of ethanol containing wash buffer can be removed from the gDNA on the glass beads by spinning them very briefly in a benchtop mini centrifuge.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method for purifying high molecular weight DNA comprising:
   (a) obtaining:
      (i) one or more centrifuge tubes for collecting fluid in a base from a bead retaining tube by centrifugation;
      (ii) one or more bead retaining tubes that have a top opening oppositely placed to one or more exit openings, and a hinged lid that can close the top opening, wherein: i. the bead containing tube accommodates 1-25 beads of the beads per ml of volume of the bead retaining tube; ii. the one or more exit openings have a diameter that is smaller than the beads and allows DNA having a median length of at least 50Kb to pass through intact into the collection tube whereby the exit opening is not in contact with the base of the centrifugation tube; and
      (iii) one or more beads that have a diameter of greater than 1 mm; and
   (b) precipitating DNA from a DNA solution that comprises the high molecular weight DNA onto 1-25 beads in a first closed end tube;
   (c) after removing liquid from the tube by aspiration and then washing the beads with a wash solution, transferring the beads into a first bead retaining tube;
   (d) with the lid closed, centrifuging the bead retaining tube positioned in the first centrifugation tube to remove any residual wash solution;
   (e) transferring the beads into a second closed end tube for adding eluant;
   (f) transferring the eluant and the beads into a second bead retaining tube; and
   (g) with the lid closed and the beads within, centrifuging the second bead retaining tube positioned in a second centrifuge tube, thereby collecting the purified high molecular weight DNA in the second centrifuge tube.

2. A method according to claim 1, wherein the top opening of the bead retaining tube has a lip that engages with the entrance of the centrifugation tube.

3. The method of claim 1, wherein the one or more beads having a shape that in one dimension has a diameter of greater than 1 mm up to 6 mm.

4. The method of claim 1, wherein the high molecular weight (HMW) DNA in the eluant has a median length of at least 50 Kb.

5. The method of claim 1, wherein the one or more beads are spherical glass beads.

6. The method according to claim 1, wherein any of the first and second of the close ended tube is the same, the first and second of the bead retaining tube and the first and second of the collection tube are the same.

7. The method of claim 1, wherein prior to (b) the method comprises agitating cells in a lysis buffer at 300-2000 rpm at a temperature in the range of 37° C.-56° C., wherein the speed of agitation determines the median length of the high molecular weight DNA precipitated on beads in (b).

8. The method of claim 1, wherein (b) further comprises washing the high molecular weight DNA precipitated on beads for removing residual non-DNA material.

9. The method of claim 1, wherein the bead retaining tubes have one or more exit openings having a diameter of less than the one or more beads, and the bead retaining tubes have designed so that the one or more beads do not block the one or more exit openings.

10. The method of claim 9, wherein the one more exit openings have a diameter of at least 0.5 mm.

\* \* \* \* \*